Dec. 29, 1936. B. A. BOURNE Plant Pat. 210
SUGARCANE
Filed Aug. 10, 1936
FIG. I
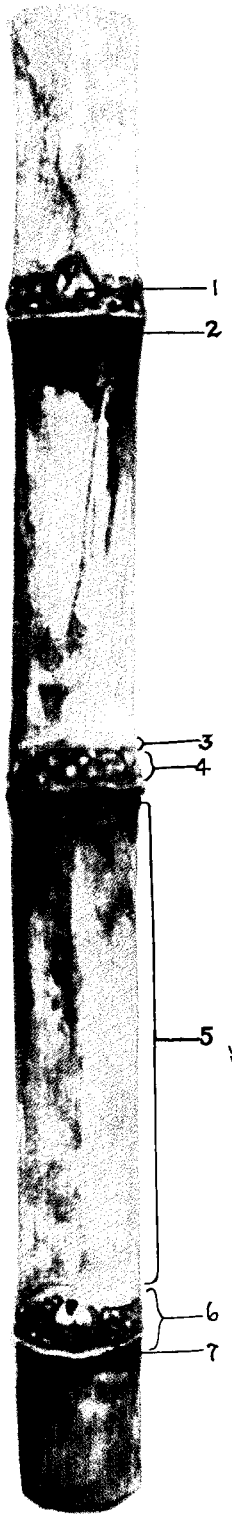
FIG. II
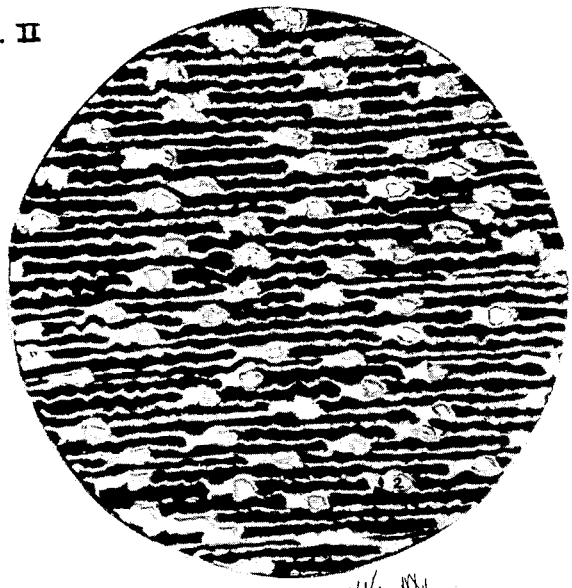
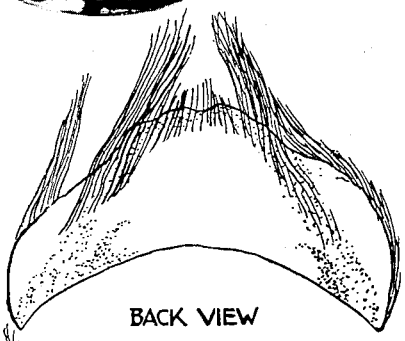
BACK VIEW
FIG. III
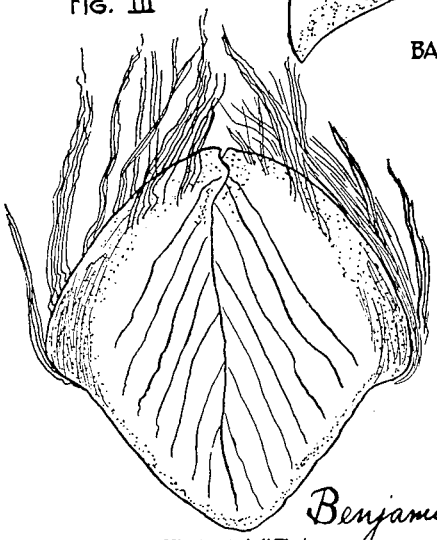
FRONT VIEW
INVENTOR
Benjamin Arthur Bourne,
By Orville M. Kile
PLANT PATENT AGENT Patented Dec. 29, 1936

Plant Pat. 210

UNITED STATES PATENT OFFICE

210

SUGARCANE

Benjamin Arthur Bourne, Clewiston, Fla.

Application August 10, 1936, Serial No. 95,223

1 Claim. (Cl. 47—59)

My new variety originated as a seedling and is the result of definite breeding efforts carried on by me in December, 1930. This variety was secured by crossing the mother cane P. O. J. 2725 with the male parent C. P. 27–108.

This variety has stalks medium to large in diameter and is early maturing. It is a good germinator, producing primary shoots early in its growth. It does not have the objectionable character of producing "suckers" late in the season which would result in immature stalks at harvest time. Because of the good stalk diameter, straightness and weight, it can be harvested at a cost per ton comparable with those which are paid for at the cheapest rate.

When planted in the Everglades of Florida during the fall or early winter, it will by the middle of November of the following year give satisfactory yields of cane sugar (sucrose) amounting to from 7 to 9 percent by weight of the cane. If not harvested in the fall (or about a year from the date of planting, if same was done in the fall) it will gradually increase in sugar (sucrose) content for from 4 to 5 months, reaching a maximum of 11 to 14 percent cane sugar (by weight of the cane), depending on soil type and weather conditions. If frozen after reaching a stage of maturity suitable for harvesting (8% cane sugar by weight), the rate of deterioration of sucrose in the stalks is markedly slow, enabling milling operations to proceed for a long period without difficulty.

As a result of studies conducted over a period of 5 years in Florida, this variety has been found to be resistant to leaf diseases due to Helminthosporium and very resistant to red-rot of the stalk (due to *Colletotrichum falcatum*) and to wind damage. It has a strong root system which prevents uprooting of stools under severe weather conditions. While not immune to mosaic disease, it is nevertheless resistant to infection, particularly on lands with a good percentage of mineral matter. Further, it has the ability to throw off the disease to a marked degree, the symptoms becoming much suppressed as the cane reaches maturity. Infected stools have been noted frequently to ratoon entirely free from the disease as indicated by leaf symptoms.

This variety has been noted to be comparatively very sensitive to boron deficiency in the soil as indicated by the typical physiological symptoms of the young leaves and growing point of stalks, resembling the so-called "pokkah boeng" disease. While these symptoms have been observed during the period of very rapid growth in June and July, no stalks have ever been observed to be killed.

When harvested from early November onwards, it exhibits good ratooning power, in spite of being frosted back several times during the winter.

The original illustration shows; "Fig. I"—mid-sections of typical stalks showing the color variations, "Fig. II"—typical structure of stem epidermis magnified 295 times, and "Fig. III"—the front and back views of a typical stem bud.

The following is a detailed description of my new variety of sugar cane.

*The Stalk*

*Structure.*—Stalks are for the most part solid in cross section and hard. When compared with other sugar canes, they are medium in fiber content.

*Growth.*—Stalks are erect from the start and remain upright, or nearly so, throughout the growth cycle. They may attain a height of from 7 to 12 feet or more, depending on soil type, weather conditions, fertilization and period of growth.

*Size.*—Diameter of stalk as measured from the middles of 20 stalks selected at random (on good "Okeechobee" type soil), varied from 2.2 centimeters to 4.0 centimeters, averaging 3.16 centimeters.

*Internodes* (Fig. I—5).—In middle of stalk frequently reach a length of 17 centimeters, but varied from 14 cms. to 21 cms., averaging from ten random measurements 15.8 centimeters. They follow one another almost in a straight line, being not at all or only very slightly "staggered".

*Nodes.*—While these are sometimes of the same diameter approximately as the internode portion, they are enlarged usually to a greater diameter, giving a characteristic appearance (as in Fig. I—6).

*Color.*—Yellow-green, sometimes with rusty-colored markings and flesh-colored tints. Typical colors and markings on middle stalk portions are shown in Fig. I.

*Furrows* (or eye grooves immediately above the eyes).—Usually present, sometimes extending even beyond the middle of the internode (Fig. I—above 1).

*Wax or "Bloom".*—Only a very slight bloom is present on surface of stem and this may fall off the lower and older portions at maturity. While a "wax ring" is commonly present, it is inconspicuous and may even be absent on the older nodes.

*Root band.*—Color is green or yellow-green to flesh-colored; shape is oblique. Width varies from 0.3 to 0.9 centimeter (Fig. I—4).

*Growth ring.*—Color is yellow to yellow-green or flesh-colored. Shape is flat, but sometimes elevated (Fig. I—3).

*Rind.*—Splitting or cracking of the rind has not been known to occur.

*Leaf scar.*—Prominent (Fig. I—7).

*Leaves*

*Blade.*—Dark green in color; width 7.5 to 9.0 centimeters across widest portion of mature outer blades. Grows somewhat upright, but with tips overhanging. Frequently curled back toward midrib near the center widest portion.

*Leaf sheath.*—Young ones usually with sharp hairs present, but old sheaths become smooth.

*Throat.*—Coated with felted hairs.

*Collar.*—The triangular areas do not meet or coalesce at the midrib. Surface with few fine hairs to waxy.

*Ligule.*—Length 0.3 centimeter. Edge fimbriate.

*Leaf stripping.*—The dead leaves and leaf sheaths usually fall away readily from the stalk at maturity, thus assisting harvesting operations without burning.

*Stem buds*

*Size.*—Good, ranging from 1.0 to 1.2 centimeters wide by 1.0 to 1.2 centimeters long.

*Position.*—Usually prominent, that is, they protrude somewhat from the surface of the stalk. The tip of the bud usually surpasses the growth ring (Fig. I—1) and the base is frequently, but not always, closely situated near the base of the leaf sheath.

*Form.*—For typical form and hair groups, see Fig. III, showing both front and back views.

*Stem epidermal cells*

The average width of epidermal cells is approximately 9.1 microns, which places the variety in a group of canes having what is considered narrow epidermal cells. The number of short-cell groups (Fig. II—1 and 2) per square millimeter is approximately 720. The number of stomata per microscopic circular field of 1.9 square millimeters is less than 1. Cork cells are rarely pointed or elongated, but are mostly characteristicially heart-shaped. No solitary cork cells (Fig. II—2) or solitary silica cells (Fig. II—1) have ever been observed to occur.

*Inflorescence*

This variety does not bloom as a rule in the Florida Everglades. Occasionally a field may show a few stalks in the pre-blooming (or "boenting") stage in late February or March, but normal tassels seldom emerge.

The principal characteristics which in combination help to distinguish my new variety from all other known varieties of sugar cane, are:

1. Early maturity.
2. Different color and shape of (*a*) stalk and (*b*) bud.
3. Different pattern of stem epidermis.
4. Upright growth habit of leaves and stalks, the middle portion of the blade frequently curling back toward the midrib.
5. High sugar-producing ability on the better as well as some of the poor types of Everglades soils.
6. Resistance to certain fungus leaf diseases common to sugar cane.
7. Strength of root system.
8. Absence of splitting of rind.
9. Size and solidity of stalk.
10. Characteristic prominence of stem buds and enlargement of the nodes.
11. Absence of tassels (inflorescence) as a rule.

Having thus disclosed my invention, what I claim as new is:

The variety of sugar cane herein shown and described, characterized particularly by its early maturity, resistance to certain leaf diseases, high sugar content, distinctive color and shape of stalk and bud, distinctive pattern of stem epidermis, and strong upright growth formed by straight stalks of fairly large diameter.

BENJAMIN ARTHUR BOURNE.